United States Patent
Detjen et al.

(10) Patent No.: US 10,696,608 B2
(45) Date of Patent: Jun. 30, 2020

(54) PROCESS FOR METHYLATING AROMATIC HYDROCARBONS

(71) Applicant: ExxonMobil Chemical Patents Inc., Baytown, TX (US)

(72) Inventors: Todd E. Detjen, Houston, TX (US); Tan-Jen Chen, Seattle, WA (US); Brett T. Loveless, Houston, TX (US); Robert G. Tinger, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/336,034

(22) PCT Filed: Sep. 12, 2017

(86) PCT No.: PCT/US2017/051179
§ 371 (c)(1),
(2) Date: Mar. 22, 2019

(87) PCT Pub. No.: WO2018/067281
PCT Pub. Date: Apr. 12, 2018

(65) Prior Publication Data
US 2019/0218159 A1    Jul. 18, 2019

Related U.S. Application Data

(60) Provisional application No. 62/405,045, filed on Oct. 6, 2016, provisional application No. 62/405,036, filed on Oct. 6, 2016.

(51) Int. Cl.
| | |
|---|---|
| *C07C 2/00* | (2006.01) |
| *C07C 2/86* | (2006.01) |
| *B01J 29/70* | (2006.01) |
| *B01J 8/02* | (2006.01) |
| *C07C 5/27* | (2006.01) |

(52) U.S. Cl.
CPC ............ *C07C 2/864* (2013.01); *B01J 8/0278* (2013.01); *B01J 29/70* (2013.01); *B01J 29/7007* (2013.01); *B01J 29/7034* (2013.01); *B01J 29/7038* (2013.01); *C07C 2/865* (2013.01); *C07C 5/2737* (2013.01); *C07C 2529/70* (2013.01); *Y02P 20/52* (2015.11)

(58) Field of Classification Search
CPC ..... C07C 2/864; C07C 15/08; C07C 2529/70; C07C 2/865; C07C 5/2737; B01J 29/70; B01J 29/7007; B01J 29/7034; B01J 29/7038; B01J 8/0278
See application file for complete search history.

(56) References Cited

U.S. PATENT DOCUMENTS

| | | | |
|---|---|---|---|
| 3,755,483 A | 8/1973 | Burress | |
| 4,002,698 A | 1/1977 | Kaeding | |
| 4,016,218 A | 4/1977 | Haag et al. | |
| 5,545,788 A | 8/1996 | Cheng et al. | |
| 5,939,597 A | 8/1999 | Dessau et al. | |
| 6,504,072 B1 | 1/2003 | Brown et al. | |
| 6,642,426 B1 | 11/2003 | Johnson et al. | |
| 7,453,018 B2 | 11/2008 | Dakka et al. | |
| 8,436,222 B2 | 5/2013 | Ghosh et al. | |
| 9,249,068 B2 * | 2/2016 | Tinger | C07C 5/277 |
| 2005/0075524 A1 | 4/2005 | Feng et al. | |
| 2012/0083637 A1 | 4/2012 | Clem et al. | |
| 2014/0128651 A1 | 5/2014 | Butler et al. | |
| 2015/0175507 A1 | 6/2015 | Bender et al. | |
| 2015/0376086 A1 | 12/2015 | Tinger et al. | |
| 2016/0221893 A1 | 8/2016 | Ravishankar et al. | |
| 2018/0099913 A1 | 4/2018 | Chen | |
| 2018/0099915 A1 | 4/2018 | Chen | |
| 2018/0170831 A1 | 6/2018 | Jan et al. | |

FOREIGN PATENT DOCUMENTS

| | | |
|---|---|---|
| CN | 2014-G33376 | 2/2014 |
| WO | 2004/000767 | 12/2003 |
| WO | 2015/094500 | 6/2015 |
| WO | 2018/067281 | 4/2018 |

OTHER PUBLICATIONS

Zhu, Z., et al., "Catalytic performance of MCM-22 zeolite for alkylation of toluene with methanol", Catalysis Today, vol. 93-95, pp. 321-325, 2004.
Yashima, T. et al.; "Alkylation on Synthetic Zeolites I. Alkylation of Toluene with Methanol", vol. 16, No. 3, (Mar. 1, 1970), pp. 273-280.

* cited by examiner

*Primary Examiner* — Sharon Pregler

(57) ABSTRACT

In a process for producing paraxylene, a hydrocarbon feedstock comprising benzene and/or toluene is contacted with an alkylating reagent comprising methanol and/or dimethyl ether in an alkylation reaction zone under alkylation conditions in the presence of an alkylation catalyst to produce an alkylated product comprising xylenes. The alkylation catalyst comprises a molecular sieve having a Constraint Index ≤5, and the alkylation conditions comprise a temperature less than 500° C. At least part of the alkylated product is supplied to a paraxylene recovery unit to recover paraxylene and produce a paraxylene-depleted stream, which is then contacted with a xylene isomerization catalyst under conditions effective to isomerize xylenes in the paraxylene-depleted stream and produce an isomerized stream having a higher concentration of paraxylene than the paraxylene-depleted stream. At least part of the isomerized stream is then recycled to the paraxylene recovery unit to recover the paraxylene therein.

23 Claims, 3 Drawing Sheets

PROCESS FOR METHYLATING AROMATIC HYDROCARBONS

CROSS-REFERENCE OF RELATED APPLICATIONS

This application is a National Phase Application claiming priority to PCT Application Serial No. PCT/US2017/051179 filed Sep. 12, 2017, which claims the benefit of U.S. Provisional Application Ser. No. 62/405,045, filed Oct. 6, 2016 and U.S. Provisional Patent Application Ser. No. 62/405,036, filed Oct. 6, 2016, both of which are hereby incorporated herein by reference in their entireties.

FIELD

This disclosure relates to a process for methylating aromatic hydrocarbons, including benzene and/or toluene, to produce xylenes and particularly paraxylene.

BACKGROUND

Benzene, toluene, and xylenes (BTX) are important aromatic hydrocarbons, for which the worldwide demand is steadily increasing. The demand for xylenes, particularly paraxylene, has increased in proportion to the increase in demand for polyester fibers and film and typically grows at a rate of 5-7% per year. Benzene is a highly valuable product for use as a chemical raw material. Toluene is also a valuable petrochemical for use as a solvent and an intermediate in chemical manufacturing processes and as a high octane gasoline component. However, in many modern aromatic complexes, some or all of the benzene and/or toluene is converted to further xylenes by either transalkylation or methylation or a combination thereof.

A major source of benzene, toluene, and xylenes (BTX) is catalytic reformate, which is produced by contacting petroleum naphtha with a hydrogenation/dehydrogenation catalyst on a support. The resulting reformate is a complex mixture of paraffins and the desired $C_6$ to $C_8$ aromatics, in addition to a significant quantity of heavier aromatic hydrocarbons. After removing the light ($C_{5-}$) paraffinic components, the remainder of reformate is normally separated into $C_{7-}$, $C_8$ and $C_{9+}$-containing fractions using a plurality of distillation steps. Liquid-liquid or extractive distillation is then typically required to remove non-aromatic co-boiling compounds from the $C_{7-}$-containing fraction before the benzene can be recovered to leave a toluene-rich fraction which is generally used to produce additional $C_8$ aromatics by either methylation or disproportionation. The $C_8$-containing fraction is fed to a xylene production loop where paraxylene is recovered, generally by adsorption or crystallization, and the resultant paraxylene-depleted stream is subjected to catalytic conversion to isomerize the xylenes back towards equilibrium distribution and to reduce the level of ethylbenzene that would otherwise build up in the xylene production loop. Transalkylation may also be added to convert at least part of the $C_{9+}$-containing fraction to additional xylenes by reaction with some of the benzene and/or toluene recovered from the $C_{7-}$-containing fraction.

While effective, these technologies are capital and variable cost intensive, and there is a general need in the industry to reduce or eliminate costs associated with upgrading the non-xylene aromatic molecules in traditional aromatic feedstocks. Furthermore, with most traditional aromatic feedstocks, the molar ratio of methyl groups to aryl groups, is less than the optimal range (1.8:1-2.2:1 on a molar basis) for maximizing the yield of xylene product per ton of feedstock. There is therefore significant interest in the development of low cost and efficient approaches to the problem of increasing xylene yields from traditional aromatics feedstocks.

U.S. Pat. No. 6,504,072 discloses a process for the selective production of paraxylene which comprises reacting toluene with methanol under alkylation conditions in the presence of a catalyst comprising a porous crystalline material having a Diffusion Parameter for 2,2 dimethylbutane of about 0.1-15 $sec^{-1}$ when measured at a temperature of 120° C. and a 2,2 dimethylbutane pressure of 60 torr (8 kPa). The porous crystalline material is preferably a medium-pore zeolite, particularly ZSM-5, which has been severely steamed at a temperature of at least 950° C. The alkylation conditions include a temperature between about 500 and 700° C., a pressure of between about 1 atmosphere and 1000 psig (100 and 7000 kPa), a weight hourly space velocity between about 0.5 and about 1000 and a molar ratio of toluene to methanol of at least about 0.2.

In addition, U.S. Pat. No. 6,642,426 discloses a process for alkylating an aromatic hydrocarbon reactant, especially toluene, with an alkylating reagent comprising methanol to produce an alkylated aromatic product, comprising: introducing the aromatic hydrocarbon reactant into a reactor system at a first location, wherein the reactor system includes a fluidized bed reaction zone comprising a temperature of 500 to 700° C. and an operating bed density of about 300 to 600 $kg/m^3$, for producing the alkylated aromatic product; introducing a plurality of streams of said alkylating reactant directly into said fluidized bed reaction zone at positions spaced apart in the direction of flow of the aromatic hydrocarbon reactant, at least one of said streams being introduced at a second location downstream from the first location; and recovering the alkylate aromatic product, produced by reaction of the aromatic reactant and the alkylating reagent, from the reactor system. The preferred catalyst is ZSM-5 which has been selectivated by high temperature steaming.

As exemplified by the U.S. patents discussed above, current processes for the alkylation of benzene and/or toluene with methanol are conducted at high temperatures, i.e., between 500 to 700° C., in the presence of a medium pore size zeolite, particularly ZSM-5. This results in a number of problems, particularly in that catalyst life per cycle is relatively short and so frequent regeneration of the catalyst is required. In addition, the existing processes typically result in significant quantities of methanol being converted to ethylene and other light olefins which reduces the yield of desirable products, such as xylenes, and increases recovery costs.

There is therefore a need for an improved process for the alkylation of benzene and/or toluene with methanol (or dimethyl ether), which increases catalyst cycle life and reduces gas make as well as facilitates integration of the process into a paraxylene production complex.

SUMMARY

According to this disclosure, it has now been found that by conducting the methylation reaction under relatively mild conditions, namely a temperature less than 500° C., in the presence of a large pore size or equivalent molecular sieve, benzene and/or toluene can be alkylated with methanol and/or dimethyl ether to produce xylenes with less light gas by-products and longer catalyst cycle life than conventional high temperature processes.

Methanol utilization (i.e., percentage conversion of methanol to xylenes) is also improved, making the process particularly attractive for integration into a paraxylene production complex.

In addition, the low temperature methylation reaction can be performed on a feedstock comprising $C_{6+}$ aliphatic hydrocarbons in addition to benzene and/or toluene, such as a $C_6/C_7$ fraction from a reformate splitter. In this way, the methylation reaction can be used to increase the volatility difference between the aromatic and aliphatic components of the feedstock, thereby eliminating or reducing the need for the liquid-liquid extraction or extractive distillation normally required to remove benzene and toluene co-boilers from conventional $C_6/C_7$ reformate fractions.

Thus, in one embodiment, a process for producing paraxylene is provided in which a hydrocarbon feedstock comprising benzene and/or toluene is contacted with an alkylating reagent comprising methanol and/or dimethyl ether in at least one alkylation reaction zone under alkylation conditions in the presence of alkylation catalyst to produce an alkylated product comprising xylenes. The alkylation catalyst comprises a molecular sieve having a Constraint Index less than or equal to 5, and the alkylation conditions comprise a temperature less than 500° C. At least part of the alkylated product is supplied to a paraxylene recovery unit to recover paraxylene from the alkylated product and produce a paraxylene-depleted stream, which is then contacted with a xylene isomerization catalyst under conditions effective to isomerize xylenes in the paraxylene-depleted stream and produce an isomerized stream having a higher concentration of paraxylene than the paraxylene-depleted stream. At least part of the isomerized stream is recycled to the paraxylene recovery unit to recover the paraxylene therein.

In another embodiment, a process for producing xylenes is provided in which a hydrocarbon feedstock comprising $C_{6+}$ aliphatic and aromatic hydrocarbons including benzene and/or toluene is contacted with an alkylating reagent comprising methanol and/or dimethyl ether in at least one alkylation reaction zone under alkylation conditions in the presence of alkylation catalyst to produce an alkylated product comprising xylenes. The alkylation catalyst comprises a molecular sieve having a Constraint Index less than or equal to 5, and the alkylation conditions comprise a temperature less than 500° C. The alkylated product may be provided to a paraxylene recovery and isomerization loop as described above.

DETAILED DESCRIPTION OF THE EMBODIMENTS

Figure 1:
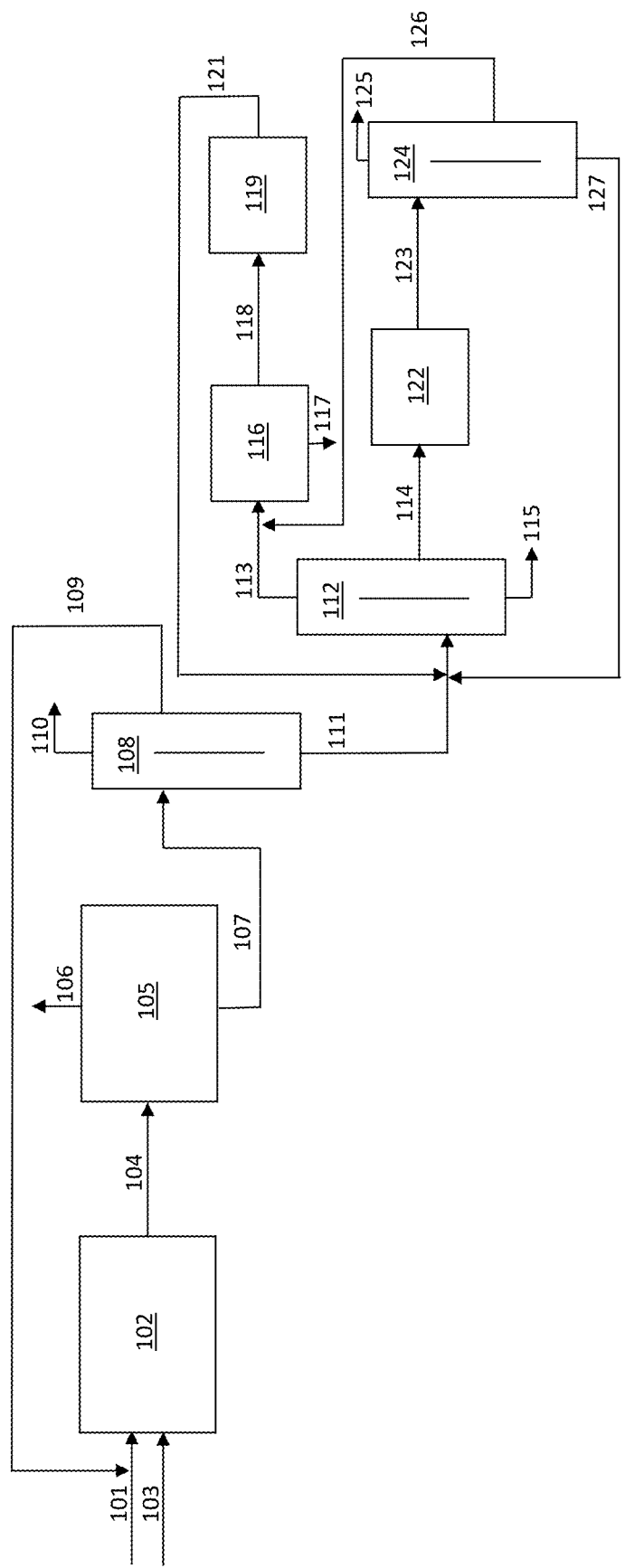
FIG. 1 is a simplified flow diagram of a process for producing paraxylene according to a first embodiment from a hydrocarbon feedstock comprising benzene and/or toluene.

The embodiments disclosed herein provide alkylation processes for producing xylenes, particularly paraxylene, that can be conducted under relatively mild conditions to produce xylenes with less light gas by-products and longer catalyst cycle life than conventional high temperature processes. Methanol utilization (i.e., percentage conversion of methanol to xylenes) is also improved. In the disclosed processes, a hydrocarbon feedstock comprising benzene and/or toluene is contacted with an alkylating reagent comprising methanol and/or dimethyl ether in the presence of alkylation catalyst under alkylation conditions. The alkylation catalyst comprises a molecular sieve having a Constraint Index less than or equal to 5 and the alkylation conditions comprise a temperature less than 500° C. The alkylated product which comprises xylenes then be supplied to a paraxylene product loop comprising a paraxylene recovery unit and a xylene isomerization unit to maximize the production of paraxylene.

As used herein, the term "$C_n$" hydrocarbon wherein n is a positive integer, e.g., 1, 2, 3, 4, 5, etc., means a hydrocarbon having n number of carbon atom(s) per molecule. The term "$C_{n+}$" hydrocarbon wherein n is a positive integer, e.g., 1, 2, 3, 4, 5, etc., means a hydrocarbon having at least n number of carbon atom(s) per molecule. The term "$C_{n-}$" hydrocarbon wherein n is a positive integer, e.g., 1, 2, 3, 4, 5, etc., as used herein, means a hydrocarbon having no more than n number of carbon atom(s) per molecule.

As used herein, the terms "alkylating" and "methylating", or "alkylation" and "methylation" may be used interchangeably.

The hydrocarbon feedstock can comprise any source of benzene, toluene or a combination of benzene and toluene. Suitable sources of benzene and toluene include catalytic reformate and steam cracked naphtha, including a heart cut benzene fraction. Suitable feedstocks can also be derived from one or more of the known gas to chemicals technologies, for example processes for the conversion of lower alkanes and alkenes, such as methane, ethane, ethylene, propane, propylene, and butane, to aromatics, processes for the conversion of methanol/DME and/or propanol to aromatics, methanol to gasoline processes, and acetylene to aromatics processes.

The feedstock can be a predominantly or entirely aromatic fraction, for example after extraction of aliphatic components present in the feedstock source by conventional liquid-liquid extraction or extractive distillation. Thus in some embodiments, the feedstock may contain more than 90 wt %, such as more than 95 wt %, for example more than 98 wt %, even more than 99 wt % benzene and/or toluene.

Alternatively, an unextracted feedstock may be used, in which the feedstock has not been subjected to liquid-liquid extraction or extractive distillation to remove the non-aromatics. The unextracted feedstock comprises $C_{6+}$ aliphatic hydrocarbons in addition to benzene and/or toluene. Thus in some embodiments, the feedstock may contain 5 wt % to 80 wt % of $C_{6+}$ aliphatic hydrocarbons, especially benzene and/or toluene co-boilers (those non-aromatics that have boiling points similar to benzene and/or toluene).

The present process comprises contacting the hydrocarbon feedstock with an alkylating reagent comprising methanol and/or dimethyl ether in at least one alkylation reaction zone in the presence of alkylation catalyst comprising a molecular sieve having a Constraint Index less than 5, such as less than 4, for example less than 3, or in some embodiments less than 2, and under alkylation conditions comprising a temperature less than 500° C. The process is effective to convert the benzene and/or toluene in the feedstock to xylenes with essentially 100% methanol conversion and substantially no light gas make. The high methanol utilization is surprising in light of the methanol utilization in the prior art toluene and/or benzene methylation processes, and results in the substantial advantages of less coke formation, which increases the catalyst life. Furthermore, in prior art processes, it is preferred to co-feed steam into the reactor with the methanol to minimize the methanol side reactions, and the steam negatively impacts catalyst life. With the nearly 100% methanol utilization in the inventive process, there is no need to co-feed steam, decreasing the energy demands of the process and increasing catalyst life.

The selectivity to xylenes in the inventive process is typically on the order of 80%, with the main by-products being benzene and $C_{9+}$ aromatics. The benzene can be separated from the alkylation effluent and recycled back to the alkylation reaction zone(s), while the $C_{9+}$ aromatics can be separated for blending into the gasoline pool or transalkylated with additional benzene and/or toluene to make additional xylenes. The life of the alkylation catalyst is enhanced as compared with existing processes since methanol decomposition is much less at the lower reaction temperature. Moreover, the use of a larger pore molecular sieve minimizes diffusion limitations and allows the alkylation to be carried out at commercially viable WHSVs.

In addition, when an unextracted feedstock is used, all or part of the benzene and/or toluene in the feedstock is converted to higher boiling aromatics, especially xylenes, and the volatility difference between the aromatic and aliphatic components of the feedstock is increased. As a result, at least part of the separation of the aliphatic component from the alkylation effluent can be achieved by conventional distillation, thereby eliminating or reducing the need for the expensive liquid-liquid extraction or extractive distillation technologies normally required to remove benzene and toluene co-boilers from mixed $C_6/C_7$ fractions.

As stated above, the catalyst employed in the present methylation process comprises a molecular sieve having a Constraint Index less than or equal to 5. In this respect, Constraint Index is a convenient measure of the extent to which a molecular sieve provides control of molecules of varying sizes to its internal structure. The method by which Constraint Index is determined is described fully in U.S. Pat. No. 4,016,218, which is incorporated herein by reference for details of the method.

Examples of suitable molecular sieves having a Constraint Index less than or equal to 5 suitable for use in the present process comprise zeolite beta, zeolite Y, Ultrastable Y (USY), Ultrahydrophobic Y (UHP-Y), Dealuminized Y (Deal Y), mordenite, ZSM-3, ZSM-4, ZSM-12, ZSM-14, ZSM-18, ZSM-20, and mixtures thereof. Zeolite ZSM-3 is described in U.S. Pat. No. 3,415,736. Zeolite ZSM-4 is described in U.S. Pat. No. 4,021,947. Zeolite ZSM-12 is described in U.S. Pat. No. 3,832,449. Zeolite ZSM-14 is described in U.S. Pat. No. 3,923,636. Zeolite ZSM-18 is described in U.S. Pat. No. 3,950,496. Zeolite ZSM-20 is described in U.S. Pat. No. 3,972,983. Zeolite Beta is described in U.S. Pat. No. 3,308,069 and Re. 28,341. Low sodium Ultrastable Y molecular sieve (USY) is described in U.S. Pat. Nos. 3,293,192 and 3,449,070. Ultrahydrophobic Y (UHP-Y) is described in U.S. Pat. No. 4,401,556. Dealuminized Y zeolite (Deal Y) may be prepared by the method found in U.S. Pat. No. 3,442,795. Zeolite Y and mordenite are naturally occurring materials but are also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

One preferred class of molecular sieve suitable for use in the present process and having a Constraint Index less than or equal to 5 are crystalline microporous materials of the MWW framework type. As used herein, the term "crystalline microporous material of the MWW framework type" includes one or more of:

molecular sieves made from a common first degree crystalline building block unit cell, which unit cell has the MWW framework topology (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084), EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et. al, in Chemical Science, 2015, Vol. 6, pp. 6320-6324) and mixtures thereof, with MCM-49 generally being preferred.

In some embodiments, the crystalline microporous material of the MWW framework type employed herein may be contaminated with other crystalline materials, such as ferrierite or quartz. These contaminants may be present in quantities ≤10 wt %, normally ≤5 wt %.

Other preferred molecular sieves for use in the present alkylation process include BEA framework type molecular sieves (such as zeolite beta) and MTW framework type molecular sieves (such as ZSM-12).

Additionally or alternatively, the molecular sieves useful herein may be characterized by a ratio of silicon to aluminum. In particular embodiments, the molecular sieves suitable herein include those having a Si/Al ratio of less than 100, preferably about 15 to 50.

In some embodiments, the molecular sieves employed herein are not subjected to pre-treatments, such as high temperature steaming, to modify their diffusion properties. In other embodiments, the molecular sieves may be selectivated, either before introduction into the aromatization reactor or in-situ in the reactor, by contacting the catalyst with a selectivating agent, such as silicon, steam, coke, or a combination thereof. In one embodiment, the catalyst is silica-selectivated by contacting the catalyst with at least one organosilicon in a liquid carrier and subsequently calcining the silicon-containing catalyst in an oxygen-containing atmosphere, e.g., air, at a temperature of 350 to 550° C. A suitable silica-selectivation procedure is described in U.S. Pat. No. 5,476,823, the entire contents of which are incorporated herein by reference. In another embodiment, the catalyst is selectivated by contacting the catalyst with steam. Steaming of the zeolite is effected at a temperature of at least about 950° C., preferably about 950 to about 1075° C., and most preferably about 1000 to about 1050° C., for about 10 minutes to about 10 hours, preferably from 30 minutes to 5 hours. The selectivation procedure, which may be repeated multiple times, alters the diffusion characteristics of the molecular sieve and may increase the xylene yield.

In addition to, or in place of, silica or steam selectivation, the catalyst may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. Further details regarding coke selectivation techniques are provided in the U.S. Pat. No. 4,117,026, incorporated by reference herein. In some embodiments, a combination of silica selectivation and coke selectivation may be employed.

It may be desirable to combine the molecular sieve, prior to selectivating, with at least one oxide modifier, such as at least one oxide selected from elements of Groups 2 to 4 and 13 to 16 of the Periodic Table. Most preferably, said at least one oxide modifier is selected from oxides of boron, magnesium, calcium, lanthanum, and most preferably phosphorus. In some cases, the molecular sieve may be combined with more than one oxide modifier, for example a combination of phosphorus with calcium and/or magnesium, since in this way it may be possible to reduce the steaming severity needed to achieve a target diffusivity value. In some embodiments, the total amount of oxide modifier present in the catalyst, as measured on an elemental basis, may be between about 0.05 and about 20 wt %, and preferably is between about 0.1 and about 10 wt %, based on the weight of the final catalyst. Where the modifier includes phosphorus, incorporation of modifier into the catalyst is conveniently achieved by the methods described in U.S. Pat. Nos. 4,356,338; 5,110,776; 5,231,064; and 5,348,643, the entire disclosures of which are incorporated herein by reference.

The above molecular sieves may be used as the alkylation catalyst employed herein without any binder or matrix, i.e., in so-called self-bound form. Alternatively, the molecular sieves may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 wt % and more usually, particularly, when the composite is prepared in the form of beads, in the range of about 2 to about 80 wt % of the composite.

The present alkylation process is conducted at relatively low temperatures, namely less than 500° C., such as less than 475° C., or less than 450° C., or less than 425° C., or less than 400° C. In order to provide commercially viable reaction rates, the process may be conducted at temperatures of at least 250° C., such as least 275° C., for example least 300° C. In terms of ranges, the process may be conducted at temperatures ranging from 250 to less than 500° C., such as from 275 to 475° C., for example from 300 to 450° C. Operating pressures will vary with temperature but generally are at least 700 kPa, for example at least 700 kPa-a, such as at least 1000 kPa-a, for example at least 1500 kPa-a, or at least 2000 kPa-a, up to about 7000 kPa-a, for example up to about 6000 kPa-a, up to about 5000 kPa-a. In terms of ranges, operating pressures may range from 700 kPa-a to 7000 kPa-a, for example from 1000 kPa-a to 6000 kPa-a, such as from 2000 kPa-a to 5000 kPa-a. Suitable WHSV values based on total aromatic and alkylating reagent feeds are in the range from 50 to 0.5 $hr^{-1}$, such as in the range from 10 to 1 $hr^{-1}$. In some embodiments, at least part of the aromatic feed, the methanol/dimethyl ether alkylating reagent and/or the alkylation effluent may be present in the alkylation reaction zone in the liquid phase.

The alkylation reaction can be conducted in any known reactor system including, but not limited to, a fixed bed reactor, a moving bed reactor, a fluidized bed reactor and a reactive distillation unit, with a fixed bed reactor being preferred. In addition, the reactor may comprise a single reaction zone or multiple reaction zones located in the same or different reaction vessels. In addition, injection of the methanol/dimethyl ether alkylating agent can be effected at a single point in the reactor or at multiple points spaced along the reactor.

The product of the alkylation reaction comprises xylenes, benzene and/or toluene (both residual and coproduced in the process), $C_{9+}$ aromatic hydrocarbons, co-produced water and in some cases unreacted methanol. It is, however, generally preferred to operate the process so that all the methanol is reacted with the aromatic hydrocarbon feed and the alkylation product is generally free of residual methanol. The alkylation product is also generally free of light gases generated by methanol decomposition to ethylene and other olefins. In some embodiments, the organic component of the alkylation product may contain at least 80 wt % xylenes.

After separation of the water, the alkylation product may be fed to a separation section, such as one or more distillation columns, to recover the xylenes and separate the benzene and toluene from the $C_{9+}$ aromatic hydrocarbon by-products. The resulting benzene and toluene may be recycled to the alkylation reaction zone, $C_{9+}$ aromatics can be recovered for blending into the gasoline pool or transalkylated with additional benzene and/or toluene to make additional xylenes.

The xylenes recovered from the alkylation product and any downstream $C_{9+}$ transalkylation process may be sent to a paraxylene production loop. The latter comprises paraxylene separation section, where paraxylene is conventionally separated by adsorption or crystallization or a combination of both and recovered. When paraxylene is separated by adsorption, the adsorbent used preferably contains a zeolite. Typical adsorbents used include crystalline alumino-silicate zeolites either natural or synthetic, such as for example zeolite X, or Y, or mixtures thereof. These zeolites are preferably exchanged by cations such as alkali or alkaline earth or rare earth cations. The adsorption column is preferably a simulated moving bed column (SMB) and a desorbant, such as for example paradiethylbenzene, paradifluorobenzene, diethylbenzene or toluene, or mixtures thereof, is used to recover the selectively adsorbed paraxylene. Commercial SMB units that are suitable for use in the inventive process are PAREX™ or ELUXYL™.

After separation of the paraxylene, the remaining paraxylene-depleted steam is fed to a xylene isomerization section which can be operated in the gas phase or the liquid phase, but in a preferred embodiment is operated in the liquid phase. Any liquid phase catalytic isomerization process known to those skilled in the art can be used in the xylene isomerization section, but one preferred catalytic system is described in U.S. Publication Nos. 2011/0263918 and 2011/0319688, the entire contents of which are incorporated herein by reference.

The conditions in the xylene isomerization section are selected so as to isomerize xylenes in the paraxylene-depleted stream, while maintaining the paraxylene-depleted stream substantially in the liquid phase, and thereby produce an isomerized stream having a higher concentration of paraxylene than the paraxylene-depleted stream. Suitable conditions for liquid phase xylene isomerization include a temperature from about 230 to about 300° C., a pressure from about 1300 to about 2100 kPa and a weight hourly space velocity (WHSV) of from about 0.5 to about 10 $hr^{-1}$. The effluent from the xylene isomerization section is then recycled to the paraxylene separation section to recover the paraxylene therein.

Referring now the drawings, FIG. 1 is a simplified flow diagram of a process for producing paraxylene according to a first embodiment. A hydrocarbon feedstock comprising benzene and/or toluene is supplied via line 101 to a low temperature methylation reactor 102, which also receives a supply of alkylating agent (methanol and/or dimethyl ether) via line 103, which may be fresh alkylating agent or recycled alkylating agent. The methylation reactor 102 includes at least one fixed bed of an alkylation catalyst, such as an MWW framework type molecular sieve, and is operated under conditions, including a temperature less than 500° C., such that the alkylating agent reacts with benzene and/or toluene in the feedstock to produce an alkylated product comprising xylenes. In addition to by-products such as $C_{9+}$ aromatics, the methylation reaction also generates water. The alkylated product will also normally contain residual benzene and/or toluene.

The alkylated product from reactor 102 is collected in line 104 and fed to a separation system 105, which may comprise one or more fractionation columns, a liquid-liquid separator, or a vapor-liquid separator, where the alkylated product is allowed to separate into an aqueous fraction containing any unreacted methanol and/or dimethyl ether and a hydrocarbon fraction containing xylenes, any unreacted benzene and/or toluene, and any aromatic by-products. The aqueous fraction is collected in line 106 and fed to a stripper (not shown) where the water is removed and the methanol and/or dimethyl ether is recovered and recycled to the reactor 102.

The hydrocarbon fraction from the separation system 105 is fed via line 107 to a distillation unit 108 where toluene is removed via line 109 and at least partly recycled to the methylation reactor 102, while the desired xylenes and heavier aromatic products are collected as a $C_{8+}$ bottoms fraction and removed via line 111. Any unreacted benzene is removed from distillation unit 108 in overhead line 110 either for recovery or recycle to the methylation reactor 102 or other parts of the process. Distillation unit 108 may be any suitable separation system known in the art, but in a preferred embodiment, distillation unit 108 is a divided wall distillation column.

The $C_{8+}$ bottoms stream in line 111 is supplied to a further distillation unit 112, such as a dividing wall distillation column, which is operated to separate the bottoms stream into a xylenes-rich $C_8$ fraction which is removed as overhead via line 113, a intermediate fraction rich in $C_9$ and $C_{10}$ aromatics which is collected in line 114, and a bottoms fraction rich in $C_{11+}$ aromatics removed via line 115.

The $C_8$ overhead fraction in line 113 is fed to a paraxylene recovery section 116, where paraxylene is conventionally separated by adsorption or crystallization or a combination of both and recovered via line 117. After recovery of the paraxylene, the remaining paraxylene-depleted steam is fed by line 118 to a xylene isomerization section 119, preferably a liquid phase xylene isomerization reactor, where metaxylene and orthoxylene in the paraxylene-depleted stream are isomerized to produce an isomerized stream having a higher concentration of paraxylene than the paraxylene-depleted stream. The effluent from the xylene isomerization section 119 is recycled via line 121 to the distillation unit 112 or to the paraxylene recovery section 116 (not shown).

The $C_9/C_{10}$ rich intermediate fraction from the distillation unit 112 is fed by line 114 to a transalkylation unit 122, which may also receive a supply of fresh $C_{9+}$ aromatic hydrocarbons, such as a $C_{9+}$ fraction from the reformate, steam cracked naphtha or other source used to provide the benzene/toluene feed in line 101. In addition, the transalkylation unit 122 may receive a supply of fresh or recycled benzene or toluene, such as part of that removed from the alkylated product by distillation column 108 and recycled via lines 110, 109 respectively. The transalkylation unit 122 is operated to convert at least part of the $C_9/C_{10}$ aromatic by-products of the methylation reaction, together with benzene and toluene, to additional xylenes. The transalkylation unit 122 can be operated in the gas phase or the liquid phase, but is preferably operated in the liquid phase. Any liquid phase catalytic transalkylation process known to those skilled in the art can be used in the transalkylation unit 122, but one preferred catalytic system is described in U.S. Provisional Application Nos. 62/313,966 and 62/313,993, the entire contents of each, which are incorporated herein by reference.

The effluent from the transalkylation unit 122 is then collected in line 123 and supplied to a further distillation unit 124, which may be a divided wall column, where the effluent is separated into a $C_{7-}$ overhead fraction, a $C_8$ intermediate fraction and a $C_{9+}$ bottoms fraction. The $C_{7-}$ fraction is removed via line 125 for recycle to the transalkylation unit 122, the methylation reactor 102, or both, while the $C_8$ fraction is fed by line 126 to the paraxylene recovery section 116 and the $C_{9+}$ fraction is fed by line 127 to the distillation unit 112.

The $C_{11+}$ containing fraction from the distillation unit 112 is supplied by line 115 to the gasoline pool, a fuel oil pool and/or to a heavy aromatics recovery unit.

Figure 2:
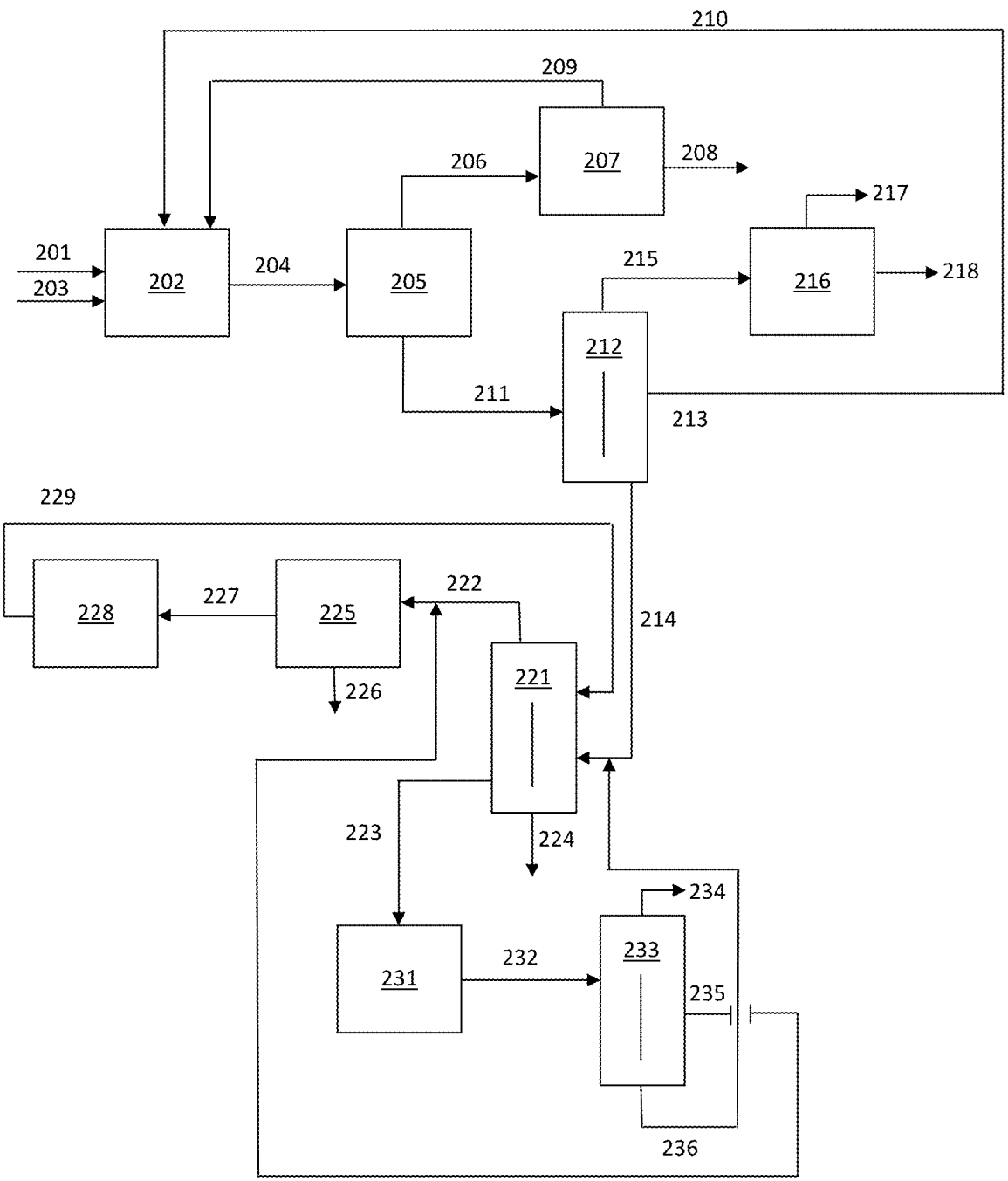
FIG. 2 is a simplified flow diagram of a process for producing paraxylene according to a second embodiment from an unextracted hydrocarbon feedstock comprising $C_{6+}$ aliphatic and aromatic components.
Figure 3:
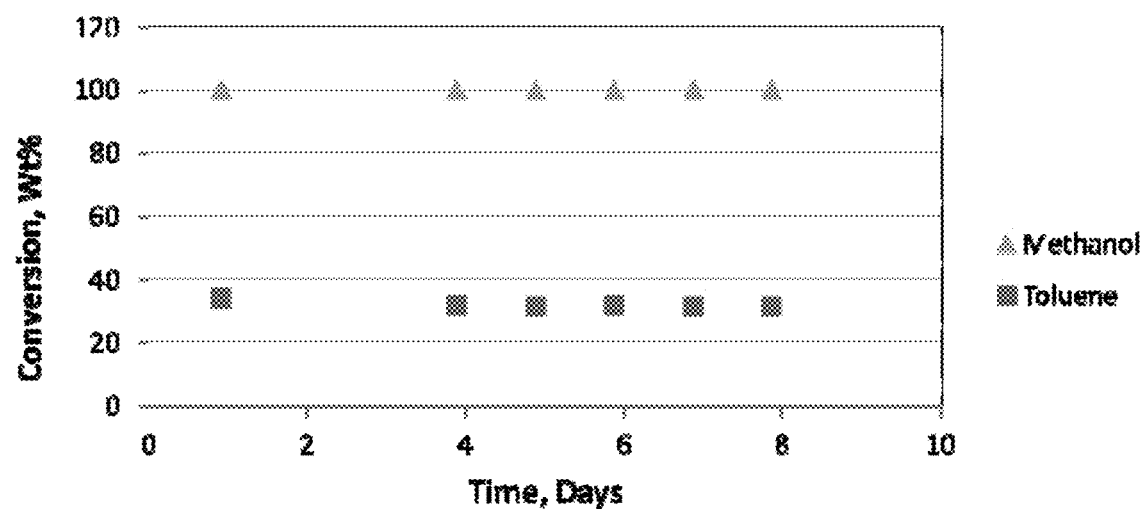
FIG. 3 is a graph of toluene and methanol conversion against time on stream in the process of alkylating toluene with methanol described in Example 1.
Figure 4:
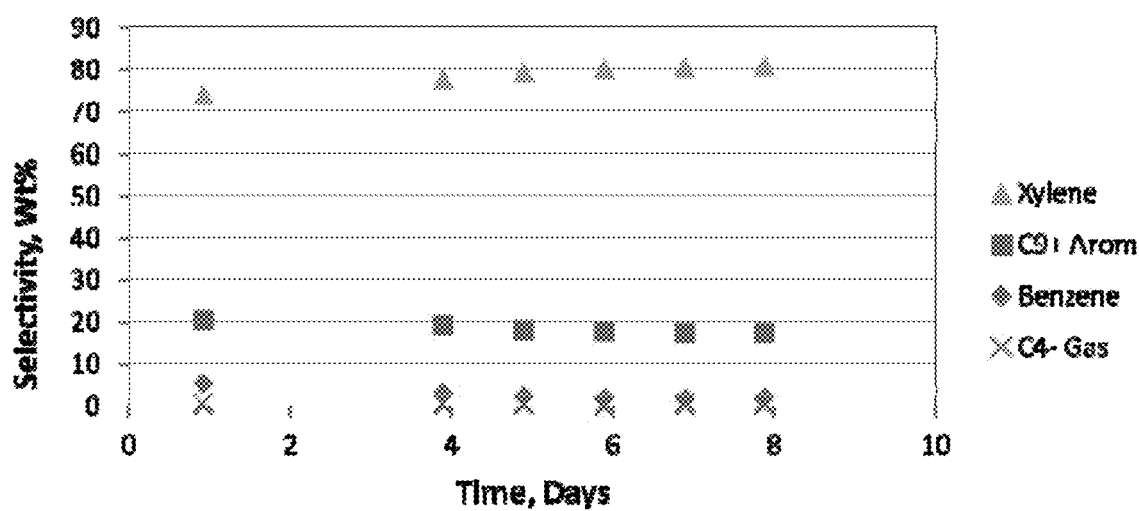
FIG. 4 is a graph of product selectivity against time on stream in the process of alkylating toluene with methanol described in Example 1.

A second embodiment is shown in FIG. 2, in which the hydrocarbon feedstock is an unextracted mixture of benzene and/or toluene and $C_6/C_7$ aliphatic compounds co-boiling with benzene and toluene. The mixed feedstock is supplied by line 201 to a low temperature methylation reactor 202, which also receives a supply of alkylating agent (methanol and/or dimethyl ether) via line 203. The methylation reactor 202 includes at least one fixed bed of an alkylation catalyst, such as an MWW framework type molecular sieve, and is operated under conditions, including a temperature less than 500° C., such that the alkylating agent reacts with benzene and/or toluene in the feedstock to produce an alkylated product comprising xylenes, $C_{9+}$ aromatic hydrocarbons, and water. The alkylated product will also normally contain residual benzene and/or toluene, together with the $C_6/C_7$ aliphatic compounds present in the original feedstock.

The alkylated product from reactor 202 is collected in line 204 and fed to a separation system 205, which may comprise one or more fractionation columns, a liquid-liquid separator, or a vapor-liquid separator, where the alkylated product is allowed to separate into an aqueous fraction containing any unreacted methanol and/or dimethyl ether and a hydrocarbon fraction containing xylenes, any unreacted benzene and/or toluene, and any aromatic by-products. The aqueous fraction is collected in line 206 and fed to a stripper 207 where the water is removed via line 208 for supply to a water treatment unit (not shown). The methanol and/or dimethyl ether in the aqueous fraction fed to the stripper 207 is recovered and recycled by line 209 to the reactor 202.

The hydrocarbon fraction from the separation system 205 is fed via line 211 to a distillation unit 212, which may be any suitable separation system known in the art, but in a preferred embodiment is a divided wall distillation column. In distillation unit 212, the toluene is removed via line 213 and at least partly recycled to the methylation reactor 202, while the desired xylenes and heavier aromatic products are collected as a $C_{8+}$ bottoms fraction and removed via line 214. The $C_6$ aliphatics and any unreacted benzene are removed from distillation unit 212 via overhead line 215 and fed to an extractive distillation or liquid-liquid extraction unit 216 where aliphatic hydrocarbons are removed via line 217 to leave a benzene-enriched stream, which is fed via line 218 either for recovery or recycle to the methylation reactor 202 or other parts of the process. In a modification (not shown), the $C_6$ aliphatics/benzene stream in line 215 can be fed to one or more further low temperature methylation reactors until all the benzene is converted to toluene and xylenes. In this way, the need for extraction of the benzene from the $C_6$ aliphatics can be completely eliminated.

The $C_{8+}$ bottoms stream in line 214 is supplied to a further distillation unit 221, such as a dividing wall distillation column, which is operated to separate the bottoms stream into a xylenes-rich $C_8$ fraction which is removed as overhead via line 222, a intermediate fraction rich in $C_9$ and $C_{10}$ aromatics which is collected in line 223, and a bottoms fraction rich in $C_{11+}$ aromatics which is removed via line 224.

The $C_8$ overhead fraction in line 222 is fed to a paraxylene recovery section 225, where paraxylene is conventionally separated by adsorption or crystallization or a combination of both and recovered via line 226. After separation of the paraxylene, the remaining paraxylene-depleted steam is fed by line 227 to a xylene isomerization section 228, preferably a liquid phase xylene isomerization reactor, where xylenes in the paraxylene-depleted stream are isomerized to produce an isomerized stream having a higher concentration of paraxylene than the paraxylene-depleted stream. The effluent from the xylene isomerization section 228 is recycled via line 229 to the distillation unit 221 or to the paraxylene recovery section 225.

The $C_9/C_{10}$ rich intermediate fraction from the distillation unit 221 is fed by line 223 to a transalkylation unit 231, which may also receive a supply of fresh $C_{9+}$ aromatic hydrocarbons, such as a $C_{9+}$ fraction from the reformate, steam cracked naphtha or other source used to provide the mixed feedstock in line 201. In addition, the transalkylation unit 231 may receive a supply of fresh or recycled benzene or toluene, such as part of that recycled via lines 218 and 213 respectively. The transalkylation unit 231 is operated, preferably in the liquid phase, to convert at least part of the $C_9/C_{10}$ aromatic by-products of the methylation reaction to additional xylenes, together with benzene and toluene.

The effluent from the transalkylation unit 231 is then collected in line 232 and supplied to a further distillation unit 233 where the effluent is separated into a $C_{7-}$ overhead fraction, a $C_8$ intermediate fraction and a $C_{9+}$ bottoms fraction. The $C_{7-}$ fraction is removed via line 234 for recycle to the transalkylation unit 231, the methylation reactor 202 or both, while the $C_8$ fraction is fed by line 235 to the paraxylene separation section 225 and the $C_{9+}$ fraction is fed by line 236 to the distillation unit 221.

The $C_{11+}$ containing fraction from the distillation unit 221 is supplied by line 224 to the gasoline pool, a fuel oil pool and/or to a heavy aromatics recovery unit.

The invention will now be more particularly described with reference to the following non-limiting Example and the accompanying drawings.

Example 1

An experiment was conducted to investigate the alkylation of toluene with methanol at a temperature of 350° C., a pressure of 600 psig (4238 kPa-a) and a WHSV of 3.5 $hr^{-1}$ based on total feed. The feed used consisted of a mixture of methanol and toluene in the weight ratio of 1:9. The catalyst used in the study is a formulated MCM-49 extrudate (80% zeolite/20% alumina binder). The reaction was carried out in a down flow fixed bed reactor. The liquid product was collected and analyzed by a 6890 Agilent GC. The gas yield was calculated by difference. The results are summarized in FIGS. 1 and 2.

As can be seen from FIG. 1, methanol conversion is essentially 100%. No methanol was detected in the product throughout the run. Toluene conversion is stable over the eight day test. Average toluene conversion is 30%, consistent with the feed composition.

Selectivity observed in the experiment is summarized in FIG. 2, from which it will be seen that the average xylene selectivity over the eight day test is at or near 80 wt %. $C_{9+}$ selectivity is about 20 wt %. Benzene selectivity is about 1.5 wt %. The gas make is estimated to be 0.5 wt %.

Example 2

Further experiments were conducted using the catalyst and reactor design discussed above in Example 1. The feed in each of these experiments was a mixture of methanol and toluene with a methanol:toluene mole ratio of 1:3. During the experiments various conditions (e.g., temperature, pressure, WHSV, etc.) were varied to determine their effect on the alkylation reaction. The results of these experiments is shown below in Table 1.

TABLE 1

| | Sample | | | | |
|---|---|---|---|---|---|
| | 1 | 2 | 3 | 4 | 5 |
| Pressure (psig) | 600 | 600 | 600 | 600 | 200 |
| Temperature (° C.) | 275 | 300 | 350 | 350 | 350 |
| WHSV (hr$^{-1}$) | 3.45 | 3.45 | 3.45 | 10.04 | 3.45 |
| Yields | | | | | |
| Methanol Conversion (%) | 94.11 | 98.09 | 100.00 | 97.91 | 95.27 |
| Toluene Conversion (%) | 0.02 | 19.49 | 29.33 | 21.18 | 7.55 |
| Xylene Selectivity (%) | 93.80 | 87.81 | 83.18 | 87.12 | 78.46 |
| Para-Xylene Selectivity (%) | 59.34 | 55.47 | 26.79 | 63.74 | 41.07 |

Referring to Samples 1, 2, and 3, it can be seen that at a constant WHSV (i.e., at 3.45 hr$^{-1}$), increasing temperature from (275° C. to 300° C. to 350° C., respectively) results in an expected drop in xylene and para-xylene selectivity, but a surprisingly large increase in both toluene and methanol conversion rates. When the reaction temperature is reduced below 250° C., conversion rates (e.g., for methanol and/or toluene) drop to such a degree such that useful production of xylenes and para-xylenes becomes unfeasible.

In addition, referring to Samples 2 and 4, when the toluene and methanol conversion is held more or less constant by increasing WHSV velocity, an increasing temperature causes a surprisingly large increase in para-xylene selectivity while overall xylene selectivity remains relatively constant.

Finally, referring to Samples 3 and 5, it can be seen that an increase in pressure from 200 psig (1379 kPa-g) to 600 psig (4137 kPa-g) appears to result in a lower para-xylene selectivity, but a substantially higher toluene conversion along with increased methanol conversion and overall xylene selectivity. Thus, in at least some embodiments, coupling an increased reaction pressure (e.g., above 200 psig) with a temperature between 250° C. and 500° C. appears to result in favorable para-xylene yields and feed conversion rates.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the example and descriptions set forth herein, but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A process for producing paraxylene, the process comprising:
   (a1) contacting a hydrocarbon feedstock comprising benzene and/or toluene with an alkylating reagent comprising methanol and/or dimethyl ether in at least one alkylation reaction zone under alkylation conditions in the presence of alkylation catalyst to produce an alkylated product comprising xylenes, wherein the alkylation catalyst comprises a molecular sieve having a Constraint Index less than or equal to 5, and wherein the alkylation conditions comprise a temperature less than 500° C. and a pressure from 700 kPa-a to 7000 kPa-a;
   (b1) supplying at least part of the alkylated product to a paraxylene recovery unit to recover paraxylene from the alkylated product and produce a paraxylene-depleted stream;
   (c1) contacting the paraxylene-depleted stream with a xylene isomerization catalyst under conditions effective to isomerize xylenes in the paraxylene-depleted stream and produce an isomerized stream having a higher concentration of paraxylene than the paraxylene-depleted stream; and
   (d1) recycling at least part of the isomerized stream to the paraxylene recovery unit to recover paraxylene from the isomerization stream.

2. The process of claim 1, wherein the alkylation conditions comprise a temperature of at least 250° C.

3. The process of claim 2, wherein the alkylation conditions comprise a temperature from 300° C. to 450° C.

4. The process of claim 1, wherein the alkylation catalyst comprises at least one molecular sieve selected from the MWW, MTW, and BEA framework types.

5. The process of claim 4, wherein the alkylation catalyst comprises at least one molecular sieve selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

6. The process of claim 5, wherein the at least one alkylation reaction zone comprises a fixed bed of the alkylation catalyst.

7. The process of claim 6, wherein the hydrocarbon feedstock comprises a refinery fraction from which aliphatic hydrocarbons have been extracted.

8. The process of claim 7, wherein the alkylated product also comprises benzene and/or toluene and the process further comprises:
   (e1) separating at least part of the benzene and/or toluene from the alkylated product prior to the supplying step (b1).

9. The process of claim 8, wherein at least part of the benzene and/or toluene separated from the alkylated product in step (e1) is recycled to the contacting step (a1).

10. The process of claim 8, wherein at least part of the benzene and/or toluene separated from the alkylated product in step (e1) is supplied to a transalkylation reaction zone which also receives a feed comprising $C_{9+}$ aromatic hydrocarbons.

11. The process of claim 10, wherein the alkylated product also comprises $C_{9+}$ aromatic hydrocarbons and the process further comprises:
(f1) separating at least part of the $C_{9+}$ aromatic hydrocarbons from the alkylated product prior to the supplying step (b1); and
(g1) supplying at least part of the $C_{9+}$ aromatic hydrocarbons separated from the alkylated product in step (f1) to the transalkylation reaction zone.

12. A process for producing xylenes, the process comprising:
(a2) providing a hydrocarbon feedstock comprising $C_{6+}$ aliphatic and aromatic hydrocarbons including benzene and/or toluene; and
(b2) contacting at least part of the hydrocarbon feedstock with an alkylating reagent comprising methanol and/or dimethyl ether in at least one alkylation reaction zone under alkylation conditions in the presence of alkylation catalyst to produce an alkylated product comprising xylenes, wherein the alkylation catalyst comprises a molecular sieve having a Constraint Index less than or equal to 5, and wherein the alkylation conditions comprise a temperature less than 500° C. and a pressure from 700 kPa-a to 7000 kPa-a.

13. The process of claim 12, wherein the alkylation conditions comprise a temperature of at least 250° C.

14. The process of claim 13, wherein the alkylation conditions comprise a temperature from 300 to 450° C.

15. The process of claim 12, wherein the alkylation catalyst comprises at least one molecular sieve selected from the MWW, MTW, and BEA framework types.

16. The process of claim 15, wherein the alkylation catalyst comprises at least one molecular sieve selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

17. The process of claim 16, wherein the at least one alkylation reaction zone comprises a fixed bed of the alkylation catalyst.

18. The process of claim 17, wherein the hydrocarbon feedstock comprises a reformate and/or a steam cracked naphtha fraction.

19. The process of claim 18 and further comprising:
(c2) fractionating at least part of the alkylated product to separate a first fraction comprising $C_{6+}$ aliphatic hydrocarbons.

20. The process of claim 19, wherein the $C_{6+}$ aliphatic hydrocarbons comprise benzene and/or toluene co-boilers.

21. The process of claim 20 and further comprising:
(d2) fractionating at least part of the alkylated product to separate a second fraction comprising xylenes;
(e2) supplying at least part of the second fraction to a paraxylene recovery unit to recover paraxylene from the second fraction and produce a paraxylene-depleted stream;
(f2) contacting at least part of the paraxylene-depleted stream with a xylene isomerization catalyst in a xylene isomerization zone under conditions effective to isomerize xylenes in the paraxylene-depleted stream and produce an isomerized stream having a higher concentration of paraxylene than the paraxylene-depleted stream; and
(g2) recycling at least part of the isomerized stream to the paraxylene recovery unit to recover paraxylene from the isomerization stream.

22. The process of claim 21, wherein the alkylated product comprises $C_{9+}$ aromatic hydrocarbons and the process further comprises:
(h2) fractionating at least part of the alkylated product to separate a third fraction comprising C9+ aromatic hydrocarbons; and
(i2) contacting at least part of the third fraction with benzene and/or toluene under transalkylation conditions such that at least part of the C9+ aromatic hydrocarbons are converted to xylenes.

23. The process of claim 22, wherein at least part of the benzene and/or toluene employed in the contacting (i2) is separated from the alkylated product.

* * * * *